United States Patent [19]

Gee

[11] Patent Number: 4,501,619

[45] Date of Patent: Feb. 26, 1985

[54] AQUEOUS EMULSIONS OF CARBOXYL-CONTAINING SILICONE FLUIDS AND A METHOD FOR THEIR PREPARATION

[75] Inventor: Ronald P. Gee, Midland, Mich.

[73] Assignee: Dow Corning Corporation, Midland, Mich.

[21] Appl. No.: 551,625

[22] Filed: Nov. 14, 1983

[51] Int. Cl.$^3$ ............................................. C09K 3/00
[52] U.S. Cl. ..................... 106/287.12; 106/287.13; 106/287.14; 106/287.16; 524/588
[58] Field of Search ............... 106/287.12, 287.13, 106/287.14, 3; 524/588; 252/313 S; 528/41

[56] References Cited

U.S. PATENT DOCUMENTS

| | | | |
|---|---|---|---|
| 2,544,194 | 7/1956 | Volkmann et al. | 106/285 |
| 3,812,201 | 5/1974 | Bey | 260/284 R |
| 4,246,029 | 1/1981 | Sanders, Jr. | 106/3 |
| 4,365,028 | 12/1982 | Leep et al. | 524/588 |
| 4,426,298 | 1/1984 | Shepley | 252/8.9 |
| 4,427,815 | 1/1984 | Ona et al. | 524/588 |

OTHER PUBLICATIONS

"Nonionic Surfactants" Schick, M. J., Mar. 18, 1971.

*Primary Examiner*—Theodore Morris
*Attorney, Agent, or Firm*—Andrew H. Ward

[57] ABSTRACT

Highly stable emulsions of carboxyl-containing silicone fluids in water are prepared by using a combination of two surfactants. The first, or primary surfactant, has the formula $RO(C_mH_{2m}O)_nH$, where R is a hydrocarbon lipophile, m has a value of 1, 2, or 3, and n has an average value greater than 15. The second or cosurfactant, is selected from fatty acid esters of sorbitol and surfactants having the formula $R'O(C_pH_{2p}O)_qH$, wherein R' is a hydrocarbon lipophile, p has a value of 1, 2, or 3 and q has a value such that the cosurfactant is just insoluble in the carboxyl-containing silicone fluid.

43 Claims, No Drawings

AQUEOUS EMULSIONS OF CARBOXYL-CONTAINING SILICONE FLUIDS AND A METHOD FOR THEIR PREPARATION

BACKGROUND OF THE INVENTION

This invention relates to aqueous emulsions of carboxyl-containing silicone fluids, and to a method of making said emulsions. The aqueous emulsions of this invention are substantially more stable than conventional emulsions of carboxyl-containing silicone fluids.

Carboxyl-containing silicone fluids are of recognized utility for a variety of applications, such as for treating textiles to make the textiles softer and more wrinkle resistant; treating human hair to make the hair glossier, softer, and more manageable; and a variety of other uses.

Many of the applications of carboxyl-containing silicone fluids require the deposition of the carboxyl-containing silicone fluid as a thin film upon a surface. Thus, it is customary to furnish the carboxyl-containing silicone fluid as an aqueous emulsion, by which it is meant herein an oil in water emulsion, or solution of the carboxyl-containing silicone fluid in an organic solvent.

Furnishing the carboxyl-containing silicone fluid as an aqueous emulsion has several important advantages over furnishing the carboxyl-containing silicone fluid as a solution. Emulsions are considered more environmentally acceptable than solutions, since the water vapor generated in a drying step is less harmful and/or toxic than vapors of organic solvent generated in a drying step. Additionally, water is less expensive than organic solvent. Finally, aqueous emulsions find particular favor in those applications, such as textile or hair treatment, wherein other treating agents used in conjunction with the carboxyl-containing silicone fluids are themselves furnished as aqueous emulsions or as water soluble salts.

Unfortunately, stability of emulsions is always a problem. With the passage of time, or upon exposure to adverse conditions such as high or low temperatures, aqueous emulsions can degrade: they can cream, i.e. form a thick white layer richer in oil than the bulk of the emulsion; they can oil, i.e. form large droplets or pools of oil; or they can "settle", i.e. liquid water can become separated from the bulk of the emulsion. In the most frequently encountered case of an oil with a lower bulk density than water, creaming and oiling are evident at the surface of the emulsion, and settling is evident at the bottom of the emulsion.

Clearly, creaming, oiling, and settling can lead to unsatisfactory results in the application of the emulsion, such as uneven application of the carboxyl-containing silicone fluid, or they can lead to total disruption of the application process.

U.S. Pat. No. 3,812,201, issued May 21, 1974, discloses an aqueous emulsion of carboxyfunctional polydiorganosiloxane fluid wherein said emulsion is stabilized by a nonionic surfactant consisting of octylphenoxypolyethoxyethanol, said surfactant having approximately ten ethoxy units. While apparently suitable for the use disclosed, similar emulsions are known to be less than satisfactory with respect to stability.

It is generally known in the art that the use of two surfactants rather than just one surfactant can help stabilize an emulsion.

Thus, U.S. Pat. No. 2,755,194, issued July 17, 1956, discloses emulsions of organopolysiloxanes substituted with monovalent hydrocarbon radicals or monovalent, halogenated hydrocarbon radicals, said emulsions being stabilized by trimethylnonylether of polyethylene glycol, a nonionic surfactant, and the sodium salt of an alkylated aryl polyether sulfate, an anionic surfactant.

U.S. Pat. No. 4,246,029, issued Jan. 20, 1981, discloses a coating composition consisting essentially of water, aminorganosiloxane, an organopolysiloxane, and a mixture of two nonionic surfactants. The first of these two nonionic surfactants is octylphenoxypolyethoxyethanol having from 1 to 13 ethoxy units, and the second nonionic surfactant is octylphenoxypolyethoxyethanol having from 6 to 40 ethoxy units.

None of the above references disclose or suggest the compositions of the present invention, which are highly stable aqueous emulsions of carboxyl-containing silicone fluids stabilized by a combination of two particular nonionic surfactants.

Copending U.S. Ser. No. 551,756, now U.S. Pat. No. 4,477,514, assigned to the assignee of the present invention, and entitled "Method For Treating Cellulosic Textile Fabrics with Aqueous Emulsions of Carboxyfunctional Silicone Fluids", describes and claims a method of using some of the compositions of the present invention.

SUMMARY OF THE INVENTION

It is an object of this invention to provide aqueous emulsions of carboxyl-containing silicone fluids having enhanced stability. It is a further object to provide emulsions of carboxyl-containing silicone fluids which can be made with a minimum of mixing energy. It is an especial object of this invention to provide emulsions of carboxyl-containing silicone fluids resistant to creaming.

These, and other objects which will be apparent to those skilled in the art upon consideration of the following specification and claims, are attained by the compositions of the present invention, which are aqueous emulsions of carboxyl-containing silicone fluids stabilized by a combination of two particular groups of nonionic surfactants.

DETAILED DESCRIPTION OF THE INVENTION

The present invention relates to an aqueous emulsion comprising
(A) from 1% to 80%, by weight, based on the total weight of the emulsion, of a carboxyl-containing silicone having the formula

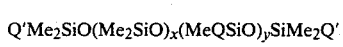

wherein
Me represents the methyl radical
Q is selected from the group consisting of carboxyalkyl radicals, carboxythioalkyl radicals, and carboxy ester radicals,
Q' is selected from the group consisting of Q radicals, Me radicals, and hydroxyl radicals,
x has an average value of from 20 to 290,
y has an average value of from 1 to 30,
(B) from 0.002% to 15%, by weight, based on the total weight of the emulsion, of a primary surfactant having the formula

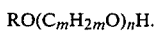

wherein
m has an average value of 1, 2, or 3,
n has an average value greater than 15,
R is a hydrocarbon lipophile,
(C) from 0.002% to 15%, by weight, based on the total weight of the emulsion, of a cosurfactant selected from the group consisting of
(i) fatty acid esters of sorbitol chosen so as to be just insoluble in said carboxyl-containing silicone, and
(ii) surfactants having the formula $$R'O(C_pH_{2p}O)_qH,$$

wherein
p has an average value of 1, 2, or 3,
q has an average value large enough to render said cosurfactant just insoluble in said carboxyl-containing silicone,
R' is a hydrocarbon lipophile, and
(D) from 10% to 98.996%, by weight, based on the total weight of the emulsion, of water; with the proviso that said primary surfactant is more hydrophilic than said cosurfactant.

The carboxyl-containing silicone fluids used in the emulsions of the present invention as component (A) have the general formula:

$$Q'Me_2SiO(Me_2SiO)_x(MeQSiO)_ySiMe_2Q'$$

wherein Me represents the methyl radical.

Q in the above formula is a carboxyl-containing radical. Q is selected from the group consisting of carboxyalkyl radicals, carboxythioalkyl radicals, and carboxy ester radicals.

Carboxyalkyl radicals are radicals containing the carboxyl group, —COOH, linked to a silicon atom by a divalent (alkylene) radical, such as methylene, ethylene, propylene, isopropylene, butylene, isobutylene, pentylene, cyclohexylene, and the like. Specific examples of carboxyalkyl radicals include: —CH$_2$COOH, —CH$_2$CH$_2$COOH, —CH$_2$CH(CH$_3$)COOH,

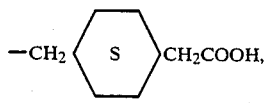

—CH$_2$CH(C$_2$H$_5$)CH$_2$COOH,
—CH$_2$CH(CH$_3$)CH(CH$_3$)CH$_2$COOH, and the like. The —CH$_2$CH(CH$_3$)COOH radical is a preferred carboxyalkyl radical in the compositions of the present invention.

Carboxythioalkyl radicals are radicals containing the carboxyl group, —COOH, linked to a silicon atom by a divalent alkyl hydrocarbon radical containing a divalent sulfur radical. Specific examples of carboxythioalkyl radicals include: —CH$_2$SCOOH, —(CH$_2$)$_2$SCOOH, —(CH$_2$)$_3$SCOOH, —CH$_2$CH(CH$_3$)SCH$_2$COOH, —CH$_2$CH$_2$SCH$_2$COOH, —CH$_2$CH(C$_2$H$_5$)SCH$_2$COOH, and the like. The —CH$_2$CH$_2$SCH$_2$COOH radical is a preferred carboxythioalkyl radical in the compositions of the present invention.

Carboxy ester radicals are radicals containing ester groups, —COOR'', linked to a silicon atom by either a divalent (alkylene) radical as hereinabove described, or by a divalent alkyl hydrocarbon radical containing a sulfur linkage as hereinabove described. The R'' group in the ester radical is a monovalent alkyl hydrocarbon having 1 to 4 carbon atoms, such as methyl, ethyl, propyl or butyl. Carboxy ester radicals in which R'' is the methyl group are preferred.

Q' in the above formula for the carboxyl-containing silicone fluid is an hydroxyl radical, Q radical as hereinabove describe, or more preferably, Q' is a methyl radical.

The value of x in the above formula is from 20 to 290. More preferably, said value of x is from 90 to 100, or from 20 to 30.

The value of y in the above formula is from 1 to 30.

Some carboxyl-containing silicone fluids as hereinabove described are available commercially. The synthesis of others from generally available starting materials is known. For example, silanes containing carboxyl groups can be prepared by reacting appropriate unsaturated carboxyl-containing compounds with silanes containing ≡SiH bonds. This reaction is catalyzed by platinum salts, as described in U.S. Pat. No. 2,723,987, issued Nov. 15, 1955, which is hereby incorporated herein by reference to teach a method for preparing carboxyl-containing silanes.

The silane starting material, containing SiH bonds, should also be selected so as to have, on average, two hydrolyzable groups bonded thereto. Such groups as halogen atoms, such as chlorine, fluorine, bromine and the like; or such groups as alkoxy groups, such as methoxy, ethoxy, propoxy and the like, are suitable hydrolyzable groups.

The silanes containing both carboxyl-containing groups and hydrolyzable groups can be hydrolyzed to form carboxyl-containing cyclosiloxanes under appropriate conditions. Said cyclosiloxanes are then copolymerized with dimethylcyclosiloxanes under well-known basic polymerization conditions.

The degree of polymerization is controlled by including an endblocker in the copolymerization. Suitable endblockers include disiloxanes having the formula (Q'Me$_2$Si)$_2$O, and Hydrolyzable silanes of the formula Q'Me$_2$SiX, wherein X represents a hydrolyzable group as hereinabove described, and Q' and Me are as hereinabove described. Thus if a degree of polymerization of 100 is desired for the carboxyl-containing silicone fluids, then 1 part, on a molar basis, of (Q'Me$_2$Si)$_2$O is included for each 98 parts, on a molar basis, of dimethylcyclosiloxanes plus carboxyl-containing cyclosiloxanes.

The primary surfactant, component (B), has the formula RO(C$_m$H$_{2m}$O)$_n$H, wherein m has an average value of 1, 2, or 3; n has an average value greater than 15, and R is a lipophile. More preferably n has a value of 40 or more.

Examples of suitable lipophiles are long chain alkyl and alkaryl residues, such as octylphenoxy, trimethylnonyl, nonylphenoxy, decylphenoxy, lauryl, cetyl, sorbitan monolaurate, and the like.

The cosurfactant, component (C) of the emulsions of the present invention, is selected from the group consisting of the fatty acid esters of sorbitol (i), and surfactants having the formula R'O(C$_p$H$_{2p}$)$_q$H(ii).

Exemplary of the fatty acid esters of sorbitol are those in which the fatty acid residue is lauric, palmitic, stearic, oleic, ricinoleic, and other well-known fatty acid residues.

Exemplary of suitable cosurfactants having the formula R'O(C$_p$H$_{2p}$O)$_q$H are those wherein: R' is a lipophile as described hereinabove for the primary surfactant; p has an average value of 1, 2, or 3; and q is selected such that the cosurfactant is just insoluble, as hereinbelow defined, in the carboxyl-containing silicone fluid.

The cosurfactant, component (C), must be just insoluble in the carboxyl-containing silicone fluid of interest. By the term "just insoluble" it is meant herein that, first, the components (A) and (C) together form a cloudy mixture; secondly, a slightly more lipophilic homologue of component (C) forms a clear mixture when dispersed in component (A).

The following experiment is an example of a procedure that would be used by one skilled in the art to select a cosurfactant that is just insoluble in the carboxyl-containing silicone fluid of interest:

First, the carboxyl-containing silicone fluid having the following formula was selected:

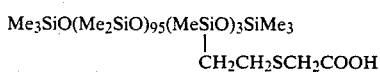

$$Me_3SiO(Me_2SiO)_{95}(MeSiO)_3SiMe_3$$
$$|$$
$$CH_2CH_2SCH_2COOH$$

Second, a series of 4 surfactants was obtained, consisting of octylphenoxypolyethyleneoxide homologues, having, on average, 1, 3, 4.5, and 10 ethylene oxide units present, respectively.

Third, a mixture of each surfactant with the carboxyl-containing silicone fluid of the above formula was made.

The mixtures of surfactant and carboxyl-containing silicone fluid wherein the surfactants contained 1, 3, and 4.5 ethylene oxide units were clear. The mixture wherein the surfactant contained 10 ethylene oxide repeat units was cloudy.

Thus the surfactant containing 10 ethylene oxide units was just insoluble in the particular carboxyl-containing silicone fluid of this experiment, and was a suitable cosurfactant for making a composition of the present invention for the particular carboxyl-containing silicone fluid in question.

Clearly, the results obtained in an experiment as described above will vary with the particular carboxyl-containing silicone fluid selected, and will vary with the hydrocarbon lipophile. However, a proper cosurfactant can be determined in each case by performing simple experiments such as those hereinabove described.

As a general guide, when the carboxyl-containing silicone fluid of interest contains 5 or 6 mole percent (MeQSiO) units, a suitable cosurfactant will have a value of q of 8 to 12. When the carboxyl-containing silicone fluid of interest contains 12 or 15 or more mole percent (MeQSiO) units, a suitable cosurfactant will have a value of q of 40 or more.

Those skilled in the art will recognize that, when dealing with nonionic surfactants as hereinabove described n and q represent average values. Thus there is a distribution of values of n and q centered around the values specified. The existence of such a distribution does not affect the stability of the compositions of the present invention, so long as the average values specified herein are adhered to.

Component (B), the primary surfactant, must also be selected so as to be more hydrophilic than component (C), the cosurfactant. Hydrophilicity is conveniently quantitized in the well known HLB, or hydrophile-lipophile balance. HLB values are empirically derived, and can be found published in manufacturer's literature, or in published texts, notably McCutcheon's Detergents and Emulsifiers, published annually by McCutcheon's Division, MC Publishing Co. PO Box 60, Ridgewood NJ 07451. HLB values increase as hydrophilicity increases. Thus component (B) must have an HLB value higher than the HLB value of component (C).

Surfactants suitable as component (B) and component (C) as hereinabove described are readily available commercially.

The water used as component (D) of the emulsions of the present invention should be relatively pure, although any water source can be used if it does not contain excessive amounts of mineral, chemical, or particulate impurities.

The respective amounts of the four components of the emulsions of the present invention are not narrowly critical, and can be adjusted appropriately for specific applications. Generally, from about 1% to about 80% component (A); from about 0.002% to about 15% component (B); from about 0.002% to about 15% component (C); and from about 10% to about 98.996% component (D) are used, all percentages being on a weight basis, based on the total weight of the emulsion.

More preferably, from about 20% to about 50% of component (A); from about 0.8% to about 10% component (B); from about 0.2% to about 5.0% component (C); and from about 35% to about 79% of component (D), are used, all percentages being on a weight basis, based on the total weight of the emulsion.

The emulsions of the present invention are made by mixing together the appropriate amounts of components (A), (B), (C), and (D), and exposing the resulting mixture to sufficient shearing forces such that component (A) becomes dispersed into particles less than about 0.5 microns in diameter.

Thus, the present invention further relates to a method for producing stable aqueous emulsions of carboxyl group containing silicone fluids, said method comprising, first, mixing together:

(A) from 1% to 80%, by weight, based on the total weight of the emulsion, of a carboxyl-containing silicone having the formula

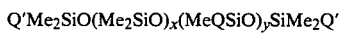

$$Q'Me_2SiO(Me_2SiO)_x(MeQSiO)_ySiMe_2Q'$$

Wherein
Me Represents the methyl radical
Q is selected from the group consisting of carboxyalkyl radicals, carboxythioalkyl radicals, and carboxy ester radicals,
Q' is selected from the group consisting of Q radicals, Me radicals, and hydroxyl radicals,
x has an average value of from 20 to 290,
y has an average value of from 1 to 30,
(B) from 0.002% to 15%, by weight, based on the total weight of the emulsion, of a primary surfactant having the formula

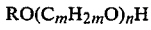

$$RO(C_mH_{2m}O)_nH$$

wherein
m has an average value of 1, 2, or 3,
n has an average value greater than 15,
R is a hydrocarbon lipophile,
(C) from 0.002% to 15%, by weight, based on the total weight of the emulsion, of a cosurfactant selected from the group consisting of (i) fatty acid esters of sorbitol chosen so as to be just insoluble in said carboxyl-containing silicone, and (ii) surfactants having the formula $$R'O(C_pH_{2p}O)_qH,$$

wherein p has an average value of 1, 2, or 3, q has an average value large enough to render said cosurfactant just insoluble in said carboxyl-containing silicone, R' is a hydrocarbon lipophile, and (D) from 10% to 98.996%, by weight, based on the total weight of the emulsion, of water; said primary surfactant being more hydrophilic than said cosurfactant, and, second, exposing the resulting mixture to sufficient shearing forces for a sufficient length of time that component (A) becomes dispersed into particles less than about 0.5 microns in diameter.

In practicing the method of the present invention, two basic techniques are contemplated for mixing the four components.

In a first technique, all four components are simply mixed together prior to exposure to shearing forces. This simple mixing can be accomplished by a mechanical mixer, or even by hand.

In a second, more preferred technique, two mixtures are made. The first mixture consists of the water, component (D), and the primary surfactant, component (B). The second mixture consists of the carboxyl-containing silicone fluid, component (A), and the cosurfactant, component (C). Each of these two mixtures is individually mixed by mechanical mixers, or by hand.

The two mixtures produced by the second technique are then combined in preparation for the second step which is exposing the mixture obtained by either the first or second mixing techniques to sufficient shearing forces.

Means for providing sufficient shearing forces are well known. Emulsification equipment, such as colloid mills, homogenizers, or sonic energy generators can be used.

The amount of shearing force that the mixture is exposed to is generally adjustable when using such equipment. For example, the gap through which the mixture is forced in using a colloid mill is adjustable. The narrower said gap is, the greater the shearing forces imposed upon the mixture. A gap setting of 0.010 inches (0.025 cm) is a representative gap setting for a colloid mill when practicing the method of the present invention.

The time of exposure to shearing forces that is sufficient to disperse component (A) in particles less than 0.5 microns in diameter can vary widely depending upon the rate at which the equipment operates relative to the total volume of mixture being emulsified. In general, a sufficient time such that the total volume of material can pass through the equipment one time is the minimum sufficient time.

Thus in a colloid mill operating at a rate of 100 liters/minute, 1 minute will be the minimum necessary time for 100 liters of mixture being emulsified.

In the case of sonic energy generators, the minimum necessary time can be determined through routine experimentation.

Exposure to sufficient shearing forces is continued until the average particle size of dispersed component (A) is less than about 0.5 micron in diameter, as measured by the particle size determination test hereinafter described.

In some cases, simply mixing by e.g. mechanical mixer, provides sufficient shear to disperse component (A) into particles less than 0.5 micron in diameter.

In a preferred embodiment of the method of the present invention, components (A), (B), and (C) are mixed, by either of the two techniques for mixing described hereinabove, with from about 1/5 to ½ of the total amount of water, component (D).

This mixture of (A), (B), (C) and part of (D) is then exposed to sufficient shearing forces for a sufficient time to disperse component (A) into particles less than about 0.5 micron in diameter. After said exposure, the remaining water, component (D) is added with simple mixing.

This preferred embodiment of the method for the present invention, allows more efficient use of equipment, and also allows higher shearing forces to be generated, since the mixture of (A), (B), (C) and part of (D) will have a higher viscosity than a mixture including all of (D).

Non-critical components can be added to the emulsions of the present invention at a suitable time, provided the nature and/or quantity of the non-critical component does not substantially destabilize the emulsion.

Examples of such non-critical components include: freeze-thaw additives, such as ethylene glycol or propylene glycol; perfumes; dyes and colorants; water soluble salts, such as catalysts, such as water soluble salts of tin and iron; antimicrobial preparations; and the like.

The emulsions of the present invention are especially useful in textile treatment processes. Their enhanced stability, especially in the presence of ionic textile treatment additives, or upon exposure to extremes of temperature, makes the emulsions of the present invention to great value in commerce. Additional benefits resulting from the enhanced stability of the emulsions of the present invention are less material rejected because of creaming, and better results in the final use for which the emulsions are intended.

In order that those skilled in the art may more fully understand the present invention, the following Examples are presented. All percentages appearing in the Examples are on a weight basis unless a different basis is specified. Me in the following Examples represents the methyl radical.

Test Procedures:

The following test procedures were used herein to evaluate the emulsions of the present invention and comparison emulsions.

Centrifuge Stability:

Dow Corning Corporate Test Method No. 0258A. Stability of an emulsion upon centrifugation was evaluated herein by placing 50 ml of the emulsion to be tested in a calibrated, 50 ml centrifuge tube. The filled tube was then centrifuged for 30 minutes at a rate of 3000 r.p.m. Upon completion of centrifugation, the tube was removed, and the emulsion therein visually inspected.

Percent cream, which is thick, white material present at the top of the tube, percent oil, which is water-free surface oil, and percent settling, which is oil-free water or substantially oil free water at the bottom of the tube, were each noted and recorded as percentages of the total volume present in the tube. Less than 1% of any of the above percents was recorded in descriptive terms, e.g., a trace of cream, none, rainbow of oil, and the like.

Heat Stability Test:

Stability of an emulsion to extended exposure to high temperatures was evaluated herein by the heat stability test. In this test, a 50 ml vial, filled with the emulsion to be tested, was tightly capped and placed in a constant temperature oven held at a temperature of 55° C. After eight days, the vial filled with emulsion was removed from the oven, and the emulsion therein was allowed to come to room temperature. Values for percent cream, percent oil, and percent settling were then visually determined as described above, and recorded.

Particle Size Determination:

Particle sizes reported herein were determined using hydrodynamic chromatography, in which a sample emulsion was pumped through a chromatography column filled with a crosslinked gel having pores of various sizes. The particles of the emulsion were thereby separated on the basis of size. The time of elution of the particles is then compared to the time of elution of standards having known particle sizes. The value of particle size thus obtained is believed to be ±10% accurate.

Materials:

The following materials were used in the appended Examples.

Carboxyl-Containing Silicone Fluids:

Carboxyl-containing silicone fluid I

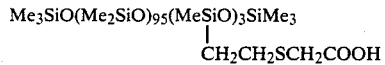

Carboxyl-containing silicone fluid II

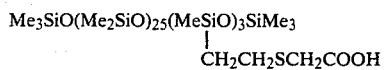

Carboxyl-containing silicone fluid III

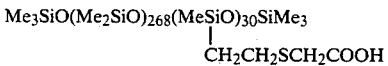

Carboxyl-containing silicone fluid IV

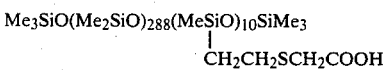

Carboxyl-containing silicone fluid V

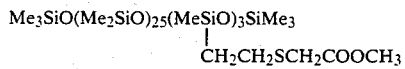

Carboxyl-containing silicone fluid VI

Carboxyl-containing silicone fluid VII

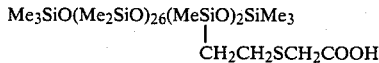

Carboxyl-containing silicone fluid VIII

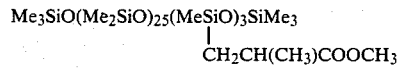

Carboxyl-containing silicone fluid IX

-continued
Carboxyl-Containing Silicone Fluids:

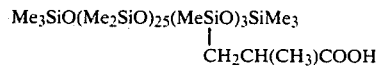

Carboxyl-containing silicone fluid X

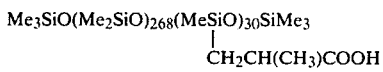

Carboxyl-containing silicone fluid XI

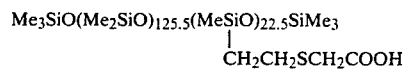

Surfactants

Surfactant I:
octylphenoxypolyethyleneoxide, there being, on average, 40 ethylene oxide units. This surfactant is provided as a 70% solution in water: Triton X-405, a product of Rohm and Haas Co., Philadelphia, PA.

Surfactant II:
trimethylnonylpolyethyleneoxide, there being, on average, 6 ethylene oxide units: Tergitol TMN-6, a product of Union Carbide Corp., New York, N.Y.

Surfactant III:
octylphenoxypolyethylene oxide, there being, on average, 10 ethylene oxide units: Triton X-100, a product of Rohm and Haas Co., Philadelphia, PA.

Surfactant IV:
sorbitan monolaurate: Arlacel 20, a product of ICI United States Inc., Wilmington, DE.

Surfactant V:
octylphenoxypolyethyleneoxide, there being, on average, 12 to 13 ethylene oxide units: Triton X-102, a product of Rohm and Haas Co., Philadelphia, PA.

Surfactant VI:
octylphenoxypolyethyleneoxide, there being, on average, 16 ethylene oxide units. This surfactant is provided as a 70% solution in water: Triton X-165, a product of Rohm and Haas Co., Philadelphia, PA.

Surfactant VII:
octylphenoxypolyethyleneoxide, there being, on average, 70 ethyleneoxide units. This surfactant is provided as a 70% solution in water: Triton X-705, a product of Rohm and Haas Co., Philadelphia, PA.

EXAMPLE 1

A mixture consisting of 350 g of carboxyl-containing silicone fluid I and 10 g of Surfactant V, (the cosurfactant) was mixed with a second mixture consisting of 104 g of water and 36 g of Surfactant I, (the primary surfactant). The subsequent mixture of 4 components was then mixed for 60 minutes by means of a mechanical stirrer. After 60 minutes of mixing, the mixture of 4 components was passed through a colloid mill with the gap set at 0.010 inches (0.025 cm). The resulting milled mixture was then mixed with 490 g of additional water, and 16 g of ethylene glycol. The resulting emulsion had the following composition:

| | |
|---|---|
| Carboxyl-containing silicone fluid I: | 35.0% |
| Surfactant V: | 1.0% |
| Surfactant I: | 3.6% |
| Water: | 59.4% |

-continued

| ethylene glycol: | 1.0% |
|---|---|

Upon centrifuge stability testing, this emulsion was observed to have a ring of cream, a rainbow of oil, drops of oil, and no settling. Particle size was found to be 0.37 microns.

EXAMPLES 2-20

The procedure of Example 1 was followed for each of the compositions described in Table 1. See Table 2 for test results. Each of these examples had particle sizes less than 0.5 micron.

Example 3 was additionally tested for heat stability. The results of heat stability testing were:
cream: none
oil: none
settling: none

TABLE 1

Compositions of Example 2-21

| Example | Carboxyl-containing silicone fluids | Primary Surfactant | | Cosurfactant | | Water | Ethylene Glycol |
|---|---|---|---|---|---|---|---|
| 2 | I | 35% | I | 3.6% | VI 1.4% | 59% | 1% |
| 3 | I | 35% | I | 3.6% | III 1.0% | 59.4% | 1% |
| 4 | I | 35% | I | 3.6% | III 1.0% | 59.4% | 1% |
| 5 | I | 35% | I | 4.4% | IV 0.54% | 59% | 1% |
| 6 | II | 35% | I | 4.4% | IV 0.54% | 59.1% | 1% |
| 7 | III | 35% | I | 4.4% | IV 0.54% | 59.1% | 1% |
| 8 | IV | 35% | I | 4.4% | IV 0.54% | 59.1% | 1% |
| 9 | V | 35% | I | 4.4% | IV 0.54% | 59.1% | 1% |
| 10 | VI | 35% | I | 4.4% | IV 0.54% | 59.1% | 1% |
| 11 | VII | 35% | I | 4.4% | IV 0.54% | 59.1% | 1% |
| 12 | VIII | 35% | I | 4.4% | IV 0.54% | 59.1% | 1% |
| 13 | IX | 35% | I | 4.4% | IV 0.54% | 59.1% | 1% |
| 14 | X | 35% | I | 4.4% | IV 0.54% | 59.1% | 1% |
| 15 | I | 35% | I | 0.55% | III 3.12% | 60.3% | 1% |
| 16 | I | 35% | I | 1.15% | III 2.70% | 60.2% | 1% |
| 17 | I | 35% | I | 1.70% | III 2.31% | 60% | 1% |
| 18 | I | 35% | I | 2.25% | III 1.93% | 59.8% | 1% |
| 19 | I | 35% | I | 2.85% | III 1.51% | 59.6% | 1% |
| 20 | I | 35% | I | 3.4% | III 1.12% | 59.5% | 1% |
| 21 | XI | 25% | VII | 3.02% | I 2.62 | 69.36% | — |

TABLE 2

Stability testing of Examples 2-21

| | | Centrifuge Stability | |
|---|---|---|---|
| Example | Cream | Oil | Settling |
| 2 | 1.5% | rainbow | — |
| 3 | none | rainbow and few drops | trace |
| 4 | — | — | — |
| 5 | none | slight rainbow | none |
| 6 | none | slight rainbow | none |
| 7 | none | none | none |
| 8 | none | none | none |
| 9 | none | none | none |
| 10 | none | none | none |
| 11 | trace | none | none |
| 12 | none | none | trace |
| 13 | none | rainbow | none |
| 14 | none | rainbow | none |
| 15 | trace | rainbow | none |
| 16 | none | slight rainbow | none |
| 17 | none | slight rainbow | none |
| 18 | none | slight rainbow | none |
| 19 | none | slight rainbow | none |
| 20 | none | oil/drops | none |
| 21 | none | none | none |

EXAMPLE 21

Fifty grams of carboxyl-containing silicone fluid XI were mixed, by a mechanical stirrer operating at a rate of 300 rpm, with a mixture consisting of 8.74 g of Surfactant VII (primary surfactant) and 12.68 g of water. The subsequent mixture was stirred approximately one hour, after which time 5.24 g of Surfactant I (cosurfactant) were added to the mixture. Stirring was continued an additional 45 minutes, after which time the average particle size of the emulsion was determined to be less than 1 micron. Stirring was continued for another hour, after which time the particle size was found to be 0.32 microns.

A portion of the above emulsion, 71.75 g, was diluted with 115.44 g of water, thereby producing an emulsion consisting of
25% carboxyl-containing silicone fluid XI
3.02% Surfactant VII
2.62% Surfactant I
69.39% water.

This emulsion showed excellent stability in the heat stability test. See Table 2 for other evaluation results.

Comparison Emulsion

In this experiment an emulsion was produced, by a procedure as generally outlined in Example 1, but using a homogenizer rather than a colloid mill. The composition of this comparison emulsion was:
carboxyl-containing silicone fluid I: 35.0%
Surfactant I: 3.6%
Surfactant II: 1.98%
Water: 59.4%
ethylene glycol: 1.0%
sodium benzoate: 0.1%
antimicrobial agent: 0.05%

This emulsion is not an embodiment of the present invention because Surfactant II is soluble, rather than just insoluble by the test outlined hereinabove.

Centrifuge stability testing resulted in 3% cream, a ring of oil, and pools of oil; no settling was observed. Heat stability testing resulted in 2% cream and oil drops being observed. A second layer of cream was also observed.

That which is claimed is:
1. An aqueous emulsion comprising a combination of
(A) from 1% to 80%, by weight, based on the total weight of the emulsion, of a carboxyl-containing silicone having the formula

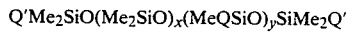
$Q'Me_2SiO(Me_2SiO)_x(MeQSiO)_ySiMe_2Q'$ wherein
Me represents the methyl radical
Q is selected from the group consisting of carboxyalkyl radicals, and carboxy ester radicals,
Q' is selected from the group consisting of Q radicals, Me radicals, and hydroxyl radicals,
x has an average value of from 20 to 290,
y has an average value of from 1 to 30,
(B) from 0.002% to 15%, by weight, based on the total weight of the emulsion, of a primary surfactant having the formula

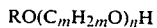
$RO(C_mH_{2m}O)_nH$ wherein
m has an average value of 1, 2, or 3, n has an average value greater than 15, R is a hydrocarbon lipophile, (C) from 0.002% to 15%, by weight, based on the total weight of the emulsion, of a cosurfactant selected from the group consisting of
  (i) fatty acid esters of sorbitol chosen so as to be just insoluble in said carboxyl-containing silicone, and
  (ii) surfactants having the formula $R'O(C_pH_{2p}O)_qH$, wherein
  p has an average value of 1, 2, or 3
  q has an average value large enough to render said cosurfactant just insoluble in said carboxyl-containing silicone,
  R' is a hydrocarbon lipophile, and (D) from 10% to 98.996%, by weight, based on the total weight of the emulsion, of water; with the proviso that said primary surfactant is more hydrophilic than said cosurfactant.

2. An emulsion as set forth in claim 1 wherein radical Q is a carboxyalkyl radical.

3. An emulsion as set forth in claim 2 wherein the carboxyalkyl radical is the —$CH_2CH(CH_3)COOH$ radical.

4. An emulsion as set forth in claim 3 wherein x has an average value of from 20 to 30 and y has an average value of from 1 to 4.

5. An emulsion as set forth in claim 4, comprising a combination of:
  from 20% to 50% by weight, based on the total weight of the emulsion, of component (A);
  from 0.8% to 10%, by weight, based on the total weight of the emulsion, of component (B);
  from 0.2% to 5%, by weight, based on the total weight of the emulsion, of component (C); and
  from 35% to 79%, by weight, based on the total weight of the emulsion, of component (D).

6. An emulsion as set forth in claim 5 wherein n has a value of from 30 to 50, and the cosurfactant is sorbitan monolaurate.

7. An emulsion as set forth in claim 3 wherein x has an average value of from 90 to 100 and y has an average value of from 1 to 4.

8. An emulsion as set forth in claim 7, comprising a combination of:
  from 20% to 50% by weight, based on the total weight of the emulsion, of component (A);
  from 0.8% to 10%, by weight, based on the total weight of the emulsion, of component (B);
  from 0.2% to 5%, by weight, based on the total weight of the emulsion, of component (C); and
  from 35% to 79%, by weight, based on the total weight of the emulsion, of component (D).

9. An emulsion as set forth in claim 8 wherein n has a value of from 30 to 50, and the cosurfactant is sorbitan monolaurate.

10. An emulsion as set forth in claim 1 wherein radical Q is a carboxythioalkyl radical.

11. An emulsion as set forth in claim 10 wherein the carboxythioalkyl radical is the —$CH_2CH_2SCH_2COOH$ radical.

12. An emulsion as set forth in claim 11 wherein x has an average value of from 20 to 30, and y has an average value of from 1 to 4.

13. An emulsion as set forth in claim 12, comprising a combination of:
  from 20% to 50% by weight, based on the total weight of the emulsion, of component (A);
  from 0.8% to 10%, by weight, base on the total weight of the emulsion, of component (B);
  from 0.2% to 5%, by weight, based on the total weight of the emulsion, of component (C); and
  from 35% to 79%, by weight, based on the total weight of the emulsion, of component (D).

14. An emulsion as set forth in claim 13 wherein n has a value of from 30 to 50 and q has a value of from 10 to 20.

15. An emulsion as set forth in claim 11 wherein x has an average value of from 90 to 100 and y has an average value of from 1 to 4.

16. An emulsion as set forth in claim 15, comprising a combination of:
  from 20% to 50% by weight, based on the total weight of the emulsion, of component (A);
  from 0.8% to 10%, by weight, based on the total weight of the emulsion, of component (B);
  from 0.2% to 5%, by weight, based on the total weight of the emulsion, of component (C); and
  from 35% to 79%, by weight, based on the total weight of the emulsion, of component (D).

17. An emulsion as set forth in claim 16 wherein n has a value of from 30 to 50 and the cosurfactant is sorbitan monolaurate.

18. An emulsion as set forth in claim 1, wherein Q is a carboxy ester radical.

19. An emulsion as set forth in claim 18, wherein the carboxy ester radical is the —$CH_2CH(CH_3)COOCH_3$ radical.

20. An emulsion as set forth in claim 19 wherein x has an average value of from 20 to 30 and y has an average value of from 1 to 4.

21. An emulsion as set forth in claim 20, comprising a combination of:
  from 20% to 50% by weight, based on the total weight of the emulsion, of component (A);
  from 0.8% to 10%, by weight, based on the total weight of the emulsion, of component (B);
  from 0.2% to 5%, by weight, based on the total weight of the emulsion, of component (C); and
  from 35% to 79%, by weight, based on the total weight of the emulsion, of component (D).

22. An emulsion as set forth in claim 19 wherein X has an average value of from 90 to 100, and y has an average value of from 1 to 4.

23. An emulsion as set forth in claim 22, comprising a combination of:
  from 20% to 50% by weight, based on the total weight of the emulsion, of component (A);
  from 0.8% to 10%, by weight, based on the total weight of the emulsion, of component (B);
  from 0.2% to 5%, by weight, based on the total weight of the emulsion, of component (C); and
  from 35% to 79%, by weight, based on the total weight of the emulsion, of component (D).

24. An emulsion as set forth in claim 23 wherein n has a value of from 30 to 50 and the cosurfactant is sorbitan monolaurate.

25. An emulsion as set forth in claim 1, comprising a combination of:
  from 20% to 50% by weight, based on the total weight of the emulsion, of component (A);

from 0.8% to 10%, by weight, based on the total weight of the emulsion, of component (B);
from 0.2% to 5%, by weight, based on the total weight of the emulsion, of component (C); and
from 35% to 79%, by weight, based on the total weight of the emulsion, of component (D).

26. An emulsion as set forth in claim 25 wherein
x has a value of from 100 to 150;
y has a value of from 20 to 30;
n has a value of from 60 to 90;
q has a value of from 30 to 50;

27. A method for producing stable aqueous emulsions of carboxyl group containing silicone fluids, said method comprising, first, mixing together:
(A) from 1% to 80%, by weight, based on the total weight of the emulsion, of a carboxyl-containing silicone having the formula $$Q'Me_2SiO(Me_2SiO)_x(MeQSiO)_ySiMe_2Q'$$

wherein
Me represents the methyl radical
Q is selected from the group consisting of carboxyalkyl radicals, carboxythioalkyl radicals, and carboxy ester radicals,
Q' is selected from the group consisting of Q radicals, Me radicals, and hydroxyl radicals,
x has an average value of from 20 to 290,
y has an average value of from 1 to 30,
(B) from 0.002% to 15%, by weight, based on the total weight of the emulsion, of a primary surfactant having the formula $$RO(C_mH_{2m}O)_nH$$

wherein
m has an average value of 1, 2, or 3,
n has an average value greater than 15,
R is a hydrocarbon lipophile,
(C) from 0.002% to 15%, by weight, based on the total weight of the emulsion, of a cosurfactant selected from the group consisting of
(i) fatty acid esters of sorbitol chosen so as to be just insoluble in said carboxyl-containing silicone, and
(ii) surfactants having the formula $$R'O(C_pH_{2p}O)_qH,$$

wherein
p has an average value of 1, 2, or 3
q has an average value large enough to render said cosurfactant just insoluble in said carboxyl-containing silicone,
R' is a hydrocarbon lipophile, and
(D) from 10% to 98.996%, by weight, based on the total weight of the emulsion, of water; said primary surfactant being more hydrophilic than said cosurfactant, and, second, exposing the resulting mixture to sufficient shearing forces for a sufficient length of time such that component (A) becomes dispersed into particles less than about 0.5 microns in diameter.

28. A method as set forth in claim 27 wherein radical Q is a carboxyalkyl radical.

29. A method as set forth in claim 28 wherein the carboxyalkyl radical is the —CH$_2$CH(CH$_3$)COOH radical.

30. A method as set forth in claim 29 wherein x has an average value of from 20 to 30 and y has an average value of from 1 to 4.

31. A method as set forth in claim 29 wherein x has an average value of from 90 to 100 and y has an average value of from 1 to 4.

32. A method as set forth in claim 27 wherein radical Q is a carboxythioalkyl radical.

33. A method as set forth in claim 32 wherein the carboxythioalkyl radical is the —CH$_2$CH$_2$SCH$_2$COOH radical.

34. A method as set forth in claim 33 wherein x has an average value of from 20 to 30 and y has an average value of from 1 to 4.

35. A method as set forth in claim 33 wherein x has an average value of from 90 to 100 and y has an average value of from 1 to 4.

36. A method as set forth in claim 27 wherein Q is a carboxy ester radical.

37. A method as set forth in claim 36 wherein the carboxy ester radical is the —CH$_2$CH(CH$_3$)COOCH$_3$.

38. A method as set forth in claim 37 wherein x has an average value of from 20 to 30, and y has an average value of from 1 to 4.

39. A method as set forth in claim 37 wherein x has an average value of from 90 to 100, and y has an average value of from 1 to 4.

40. A method as set forth in claim 27 wherein there is combined:
from 20% to 50% by weight, based on the total weight of the emulsion, of component (A);
from 0.8% to 10%, by weight, based on the total weight of the emulsion, of component (B);
from 0.2% to 5%, by weight, based on the total weight of the emulsion, of component (C); and
from 35% to 79%, by weight, based on the total weight of the emulsion, of component (D).

41. A method as set forth in claim 40 wherein:
x has a value of from 20 to 30;
y has a value of from 1 to 4;
n has a value of from 30 to 50; and the cosurfactant is sorbitan monolaurate.

42. A method as set forth in claim 40 wherein:
x has a value of from 90 to 100;
y has a value of from 1 to 4;
n has a value of from 30 to 50; and the consurfactant is sorbitan monolaurate.

43. A method as set forth in claim 40 wherein:
x has a value of from 100 to 150;
y has a value of from 20 to 30;
n has a value of from 60 to 90; and
q has a value of from 30 to 50.

* * * * *

UNITED STATES PATENT AND TRADEMARK OFFICE
CERTIFICATE OF CORRECTION

PATENT NO. : 4,501,619

DATED : February 26, 1985

INVENTOR(S) : Ronald Paul Gee

It is certified that error appears in the above-identified patent and that said Letters Patent is hereby corrected as shown below:

1. In Column 3, line 12, the word "R'O($C_pH_{2p}$O)qH" should read "R'O($C_pH_{2p}$O)$_q$H"

2. In Column 4, line 6, the word "describe" should read "described"

3. In Column 4, line 18, the word "SiH" should read " SiH"

4. In Column 4, line 39, the word "Hydrolyzable" should read "hydrolyzable"

5. In Column 4, line 66, the word "R'O(CpH$_{2p}$O)$_q$H" should read "R'O($C_pH_{2p}$O)$_q$H"

6. In Column 6, line 44, the word "Wherein" should read "wherein"

7. In Column 6, line 45, the word "Represents" should read "represents"

8. In Column 8, line 35, the word "to" should read "of"

9. In Column 10, line 23, the word "Triton" should read "TRITON"

10. In Column 10, line 27, the word "Tergitol" should read "TERGITOL"

11. In Column 10, line 31, the word "Triton" should read "TRITON"

12. In Column 10, line 34, the word "Arlacel" should read "ARLACEL"

13. In Column 10, line 38, the word "Triton" should read "TRITON"

UNITED STATES PATENT AND TRADEMARK OFFICE
CERTIFICATE OF CORRECTION

PATENT NO. : 4,501,619

DATED : February 26, 1985

INVENTOR(S) : Ronald Paul Gee

It is certified that error appears in the above-identified patent and that said Letters Patent is hereby corrected as shown below:

14. In Column 10, line 43, the word "Triton" should read "TRITON"

15. In Column 10, line 48, the word "Triton" should read "TRITON"

16. In Column 11, Table 1, the word "Example" should read "Examples" in the heading.

17. In Column 11, Table 1, the word under Cosurfactant Example 21 "2.62" should read "2.62%".

18. In Column 12, line 56, the words after "radicals," and before "and" insert "carboxythioalkyl radicals,".

Signed and Sealed this

Twenty-seventh Day of May 1986

[SEAL]

Attest:

DONALD J. QUIGG

Attesting Officer

Commissioner of Patents and Trademarks